United States Patent [19]

Roucher et al.

[11] Patent Number: 5,279,561
[45] Date of Patent: Jan. 18, 1994

[54] DILITATION CATHETER

[75] Inventors: Leo Roucher; Erich Wolf, both of Escondido, Calif.

[73] Assignee: Medtronic, Inc., Minneapolis, Minn.

[21] Appl. No.: 832,664

[22] Filed: Feb. 5, 1992

Related U.S. Application Data

[63] Continuation of Ser. No. 495,259, Mar. 16, 1990, abandoned.

[51] Int. Cl.$^5$ .................................................. A61M 25/00
[52] U.S. Cl. ........................................ 604/96; 606/194
[58] Field of Search ........................................ 604/96–; 128/657, 772; 606/191, 192

[56] References Cited

U.S. PATENT DOCUMENTS

| | | | |
|---|---|---|---|
| 4,020,829 | 5/1977 | Willson et al. | 604/95 |
| 4,665,475 | 8/1984 | Mardorf et al. | 604/155 |
| 4,723,936 | 2/1988 | Buchbinder et al. | 604/96 |
| 4,771,778 | 9/1988 | Mar | 606/192 |
| 4,821,722 | 4/1989 | Miller et al. | 604/96 |
| 4,886,067 | 12/1989 | Palermo | 128/657 |
| 5,002,559 | 3/1991 | Tower | 128/772 |
| 5,135,487 | 8/1992 | Morrill et al. | 604/96 |

*Primary Examiner*—C. Fred Rosenbaum
*Assistant Examiner*—Chalin Smith
*Attorney, Agent, or Firm*—Dianne M. F. Plunkett; Harold R. Patton

[57] ABSTRACT

A dilatation catheter comprimising a torque-transmitting shaft, a flexible body surrounding the shaft, and an inflatable balloon having a proximal end mounted on the flexible body. The dilatation catheter also includes a tip spring having a proximal end fixedly mounted to the shaft proximal to the distal end of the balloon and a distal end fixedly attached to the distal tip of the shaft. The dilatation catheter further comprises a tip tube having a proximal end fixedly mounted to the shaft and a distal end exending through the distal end of the balloon, the distal end of the balloon being fixedly attached to the tip tube, the tip tube being sufficiently flexible and the proximal end being sufficiently removed from the distal end of the balloon so that rotation of the shaft causes rotation of the tip substantially without twisting the balloon and substantially reducing rotation of the tip spring where it contacts the vascular system.

11 Claims, 1 Drawing Sheet

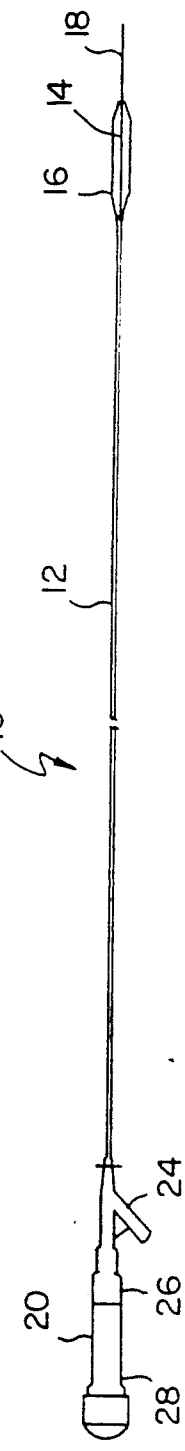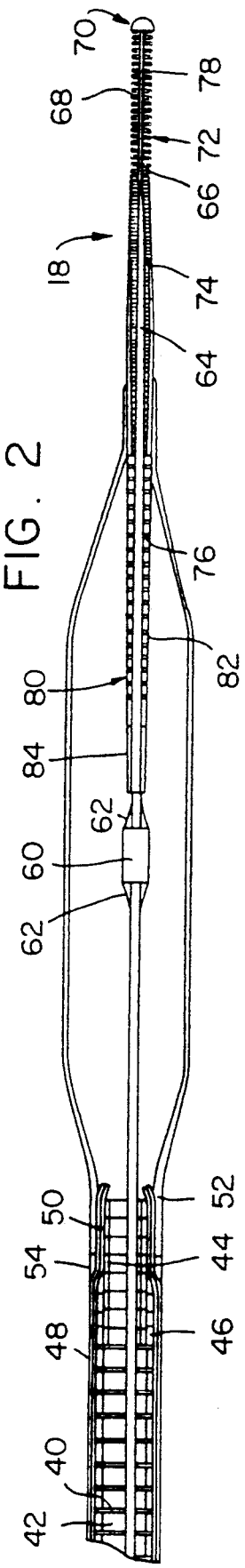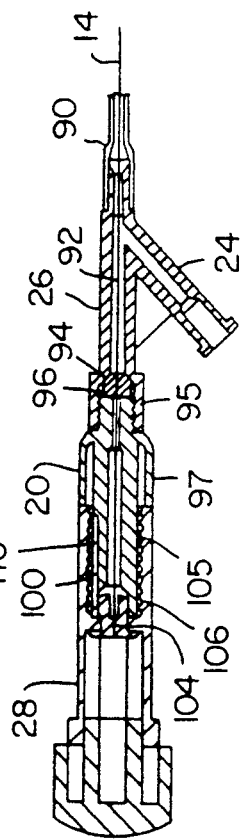

DILITATION CATHETER

This is a continuation of application Ser. No. 07/495,259 filed Mar. 16, 1990, now abandoned.

BACKGROUND OF THE INVENTION

1. Field of the Invention

This invention relates to medical catheters, particularly those for opening lesions in arteries.

Catheters designed for steering through a tortuous path of small arteries, such as the coronary arteries, have been of two general types. One type slides over a separate guidewire. The second type involves a guidewire built into the catheter. The guidewire and catheter are inserted in the artery as a unit.

Such catheters built on a wire are steered through the arteries by directing a bent tip in the proper direction to enter a branch. The guidewire is rotated to turn the bent tip in the proper direction. A known problem in the prior art on-the-wire catheters is that rotation of the guidewire may cause the balloon in the catheter to twist and wrap up around the guidewire. This will cause later problems in inflation and deflation of the balloon.

This problem is taught in U.S. Pat. No. 4,664,113 which explains the problems with balloon wrap. That patent discloses a typical prior art device where the distal end of the balloon is fixed directly to the guidewire. When the guidewire rotates, the balloon twists. In an attempt to mitigate this problem, that patent limited rotation of the wire. Such limitations on rotation are well known in other catheter arts, but is found to be necessary for a particular functional purpose in wires of the type disclosed with a balloon bonded directly to a guidewire. What is needed in the art is a balloon structure which performs the functions of traditional on-the-wire catheters, but is not subject to the balloon wrap problem of the style in U.S. Pat. No. 4,664,113.

One other attempt to solve this problem is a design such as the PROBE catheter from USCI. This has a guidewire independent of the end of the balloon. However, the device does not have sufficient structural integrity for retaining the guidewire relative to the catheter structure. A structure is needed which prevents wrap but which is structurally sound and preserves the integrity of the tip area.

SUMMARY OF THE INVENTION

A catheter constructed according to the present invention involves a torque transmitting shaft, a flexible catheter body having a lumen for passage of the shaft, a balloon mounted on the distal end of the catheter body; a flexible tubing extending from within the balloon out to a distal tip of the catheter; the flexible tubing being bonded to the distal end of the balloon so that the shaft is free to move relative to the distal end of the balloon.

In the preferred embodiment the flexible tubing includes a spring covered by a tip tube. The spring attached at its proximal end and distal ends to the shaft.

BRIEF DESCRIPTION OF THE DRAWINGS

FIG. 1 is a side plan view of a catheter constructed according to the present invention partially broken way.

FIG. 2 is a cross sectional view of a distal portion of the catheter of FIG. 1.

FIG. 3 is a cut-away, partially cross sectional, view of a proximal section of the catheter of FIG. 1, including the manifold.

DETAILED DESCRIPTION OF THE DRAWINGS

The catheter 10 constructed according to the present invention includes a flexible catheter body 12, a torque transmitting shaft 14, a balloon 16, a flexible tip 18 and a manifold or handle 20. Handle 20 includes an arm 24 for mounting balloon inflation equipment and a second arm 26 for guidewire mounting. A rotatable handle 28 is mounted for rotation within arm 26.

As shown in FIG. 2, catheter body 12 includes a body spring 40 which is a spring wound of metal of a rectangular cross section. Body springs of prior art devices such as the Versaflex Omniflex catheter are suitable. Body spring 40 forms a lumen 42 through which passes shaft 14. Mounted within lumen 42 is a smaller diameter stainless steel spring 44 which is brazed to body spring 40 at braze 46.

In the illustrated embodiment, body spring 40 has an outside diameter of 0.03 inches. Spring 44 has an outside diameter of 0.026 inches.

Flexible plastic tubing 48 is mounted over body spring 40, as in the prior art Omniflex device. In the preferred embodiment, tube 48 is made of polyethylene shaft stock.

Tubing 48 is tapered at its distal section 50 where it narrows to fit over spring 44. Balloon 16 has a proximal section 52 mounted over the tapered section 50 of tube 48. Spring 44 is attached to tube 48 by adhesive. In the preferred embodiment, section 52 of balloon 16 is cut off with a square non-tapered end. The section 50 of tube 48 which is not covered by balloon portion 52 is filled in with adhesive 54 to make a smooth external surface of the outside diameter of tube 48. Balloon proximal portion 52 and adhesive 54 are generally equal in diameter. In the preferred embodiment, adhesive 54 is an ultraviolet cured adhesive.

A radiopaque marker band 60 is mounted within balloon 16 on shaft 14, preferably by brazing. Marker 60 is made and attached using common prior art techniques. Marker 60 is preferably a platinum cylinder, but may be platinum wire wound around shaft 14. In order to have a smooth transition from shaft 14 to marker 60, a ramp of adhesive 62 is formed at either end of the marker 60. In the preferred embodiment, adhesive 62 is cyanoacrylate.

Shaft 14 has a tapered section 64 and a flattened tip 66. Mounted on flattened tip 66 by brazing is a flat ribbon wire 68. A metallic tip 70 is brazed to the tip of flat wire 68.

A tip spring 72 is mounted over shaft 14. Tip spring 72 has a tightly coiled medial section 74, a spread flexible proximal section 76 and a spread flexible distal section 78. The proximal end of section 76 is brazed to shaft 14 at 80. Distal section 78 is brazed to tip 70. Therefore, spring 72 is fixed at either end but flexes throughout the rest of its structure. A tip tube 82 is mounted over spring 72. Tube 82 is attached to shaft 14 by adhesive 84, which in the preferred embodiment is cyanoacrylate. This seals the interior of tube 82 from the interior of balloon 16. Tip tube 82 extends distally through the distal end 84 of balloon 16. Distal end 84 of balloon 16 is bonded to tube 82 by adhesive, which in the preferred embodiment is an ultraviolet cured. In turn, tube 82 is heat shrunk to spring 72 adhesive.

The structure of catheter 10 provides a free moving guidewire within spring 72 so that the catheter is not susceptible to balloon wrap. When shaft 14 is rotated, it moves freely within lumen 42 of body spring 40 and within tip spring 72. If shaft 14 is overturned by the user of the catheter, the torque is taken up in spring 72 and not transmitted to balloon 16. Both proximal section 76 and distal section 78 of tip spring 72 are loosely wound springs which will absorb the torquing effect. This allows multiple turns of shaft 14 without affect on balloon 16.

As a reminder to the physician to return shaft 14 to the center position, means are provided to indicate the number of turns made. In manifold 20, shaft 14 is attached to strain relief means 90. Shaft 14 continues through lumen 92 through silicone seal 94. A threaded lumen 95 has female threads 96. Guidewire housing 97 has male threads which mate with threads 96. The interacting threads squeeze silicone seal 94 to prevent backflow of fluid out of lumen 92.

Guidewire housing 97 has a longitudinal groove 100 which has a semicircular cross section. Rotatable handle 28 is mounted over second housing 97. Rotatable handle 28 is held to guidewire housing 97 by spring clip 104. Rotatable handle 28 has a bore 105 which is cut with helical threads 106. The cross section of helical thread 106 is a semicircle matching in diameter the cross section of longitudinal groove 100. A ball 110 is mounted to ride within groove 100 and helical threads 106. As rotatable handle 28 is turned relative to guidewire housing 97, ball 110 follows helical grooves 106 and moves, correspondingly, up and down longitudinal groove 100. When ball 110 reaches an end of groove 100, handle 28 can no longer rotate in that direction. Therefore, the amount of turn of rotatable handle 28 relative to housing 97 depends on the number of turns of helical groove 106.

In the embodiment illustrated, there can be four turns in either direction of handle 28. Although balloon twist does not occur in the design illustrated, the limitation on rotation reminds the physician that rotation has occurred in one direction and that further rotation in that direction could cause spring compression in the tip section.

We claim:

1. A catheter comprising:
a torque transmitting shaft having a tip;
a flexible body surrounding the shaft;
an inflatable balloon having a proximal end and a distal end, the proximal end mounted on the flexible body;
a tip tube surrounding the shaft, the tip tube having a first end fixedly mounted to the shaft proximal to the distal end of the balloon, the tip tube also having a second end extending to the distal end of the balloon wherein the distal end of the balloon is fixedly mounted to the tip tube; and
a tip spring having a proximal end fixedly mounted to the shaft within the tip tube.

2. A catheter comprising:
a torque transmitting shaft having a distal end and a proximal end and comprised of a core wire extending the length of the character;
a flexible body surrounding the shaft;
an inflatable balloon having a proximal end and a distal end, the proximal end mounted on the flexible body;
a tip tube surrounding the shaft, the tip tube having a first end fixedly mounted to the shaft proximal to the distal end of the balloon and having a second end fixedly mounted to the distal end of the balloon wherein the tip tube is sufficiently flexible so that rotation of the shaft causes rotation of the tip while minimizing twisting of the balloon; and
a tip spring having a proximal end fixedly mounted to the shaft proximal to the distal end of the balloon and a distal end attached to the distal tip of the shaft.

3. A catheter comprising:
a torque transmitting shaft having a distal end and a proximal end and comprised of a core wire extending the length of the catheter;
a flexible body surrounding the shaft;
an inflatable balloon having a proximal end and a distal end, the proximal end mounted on the flexible body;
a tip tube surrounding the shaft, the tip tube having a first end fixedly mounted to the shaft proximal to the distal end of the balloon and having a second end fixedly mounted to the distal end of the balloon wherein the tip tube is sufficiently flexible so that rotation of the shaft causes rotation of the tip while minimizing twisting of the balloon;
a housing having a first body with a male segment with a longitudinal groove;
a second body portion mounted for rotational movement about the male portion of the first body, the second body having a helical groove; and
a ball means mounted for movement along the helical groove and along the longitudinal slot so that movement of the first body relative to the second body is stopped when the ball reaches the end of the slot.

4. A catheter comprising:
a torque transmitting shaft having a tip;
a flexible body surrounding the shaft;
an inflatable balloon having a proximal end and a distal end, the proximal end mounted on the flexible body;
a tip tube surrounding the shaft, the tip tube having a first end fixedly mounted to the shaft proximal to the distal end of the balloon, the tip tube also having a second end extending beyond the distal end of the balloon wherein the distal end of the balloon is fixedly mounted to the tip tube and the tip tube is sufficiently flexible so that rotation of the shaft causes rotation of the tip while minimizing twisting of the balloon; and
wherein the shaft is comprised of a core wire extending the length of the catheter.

5. A catheter comprising:
a torque transmitting shaft having a tip;
a flexible body surrounding the shaft;
an inflatable balloon having a proximal end and a distal end, the proximal end mounted on the flexible body;
a tip tube surrounding the shaft, the tip tube having a first end fixedly mounted to the shaft proximal to the distal end of the balloon, the tip tube also having a second end extending beyond the distal end of the balloon wherein the distal end of the balloon is fixedly mounted to the tip tube and the tip tube is sufficiently flexible so that rotation of the shaft causes rotation of the tip while minimizing twisting of the balloon; and a tip spring having a proximal end fixedly mounted to the shaft proximal to the distal end of the balloon and a distal end fixedly attached to a distal tip of the shaft so that rotation of the catheter causes rotation of the tip while reducing rotation of the spring where it contacts the vascular system.

6. A catheter with limited shaft rotation comprising:
a torque-transmitting shaft;
a flexible body surrounding the shaft;
a housing comprising
- a first body with a male segment having a longitudinal slot,
- a second body mounted on the shaft for rotation about the first body, the second body having a helical groove therein;
- a ball means mounted for movement in the helical groove and the slot so that movement of the second body relative to the first is stopped when the ball means reaches the end of the slot;

an inflatable balloon having a proximal end mounted on the flexible body;
a tip spring having a proximal end fixedly mounted to the shaft proximal to the distal end of the balloon and a distal end fixedly attached to a distal tip of the shaft; and
a tip tube having a proximal end fixedly mounted to the shaft and a distal end extending through the distal end of the balloon, the distal end of the balloon being fixedly attached to the tip tube, the tip tube being sufficiently flexible and the proximal end being sufficiently removed from the distal end of the balloon so that the rotation of the shaft causes rotation of the tip substantially without twisting the balloon and while reducing rotation of the tip spring where it contacts the vascular system.

7. A dilatation catheter comprising:
a torque transmitting shaft;
a flexible body surrounding the shaft;
an inflatable balloon having a proximal end mounted on the flexible body;
a tip spring having a proximal end fixedly mounted to the shaft proximal to the distal end of the balloon and a distal end fixedly attached to a distal tip of the shaft; and
a tip tube having a proximal end fixedly mounted to the shaft and a distal end extending through the distal end of the balloon, the distal end of the balloon being fixedly attached to the tip tube the tip tube being sufficiently flexible and the proximal end being sufficiently removed from the distal end of the balloon so that rotation of the shaft causes rotation of the tip substantially without twisting the balloon and substantially without rotation of the tip spring.

8. The catheter of claim 7 further comprising a housing having a first body with a male segment with a longitudinal groove;
a second body portion mounted for rotational movement about the male portion of the first body, the second body having a helical groove; and
a ball means mounted for movement along the helical groove and along the longitudinal slot so that movement of the first body relative to the second body is stopped when the ball reaches the end of the slot.

9. A catheter according to claim 7 and wherein the flexible body is formed of one or more spring coils.

10. A catheter according to claim 7 and wherein the tip spring is formed of at least one stretched portion and at least one unstretched portion.

11. A catheter according to claim 7 and wherein the shaft has only one continuous taper to a flat tip.

* * * * *

UNITED STATES PATENT AND TRADEMARK OFFICE
CERTIFICATE OF CORRECTION

PATENT NO. : 5,279,561
DATED : January 18, 1994
INVENTOR(S) : Leo Roucher, Erich Wolf It is certified that error appears in the above-indentified patent and that said Letters Patent is hereby corrected as shown below:

Col. 3, line 64, "character" should be --catheter--.

Col. 6, line 17, "without" should be --reducing--.

Col. 6, line 18, add --where it contacts the vascular system-- after "spring".

Signed and Sealed this

Nineteenth Day of July, 1994

*Attest:*

BRUCE LEHMAN

*Attesting Officer*   *Commissioner of Patents and Trademarks*